United States Patent
Moggridge (10) Patent No.: US 9,528,932 B2
(45) Date of Patent: Dec. 27, 2016

(54) INTEGRATING SPHERE TYPE DEVICE WITH SPECULAR CONTROL

(71) Applicant: Westboro Photonics, Ottawa, Ontario (CA)

(72) Inventor: Tim Moggridge, Ottawa (CA)

(73) Assignee: Westboro Photonics, Ottawa, Ontario (CA)

( * ) Notice: Subject to any disclaimer, the term of this patent is extended or adjusted under 35 U.S.C. 154(b) by 0 days.

(21) Appl. No.: 14/761,378

(22) PCT Filed: Jan. 16, 2014

(86) PCT No.: PCT/CA2014/000026
§ 371 (c)(1),
(2) Date: Jul. 16, 2015

(87) PCT Pub. No.: WO2014/110664
PCT Pub. Date: Jul. 24, 2014

(65) Prior Publication Data
US 2015/0355087 A1 Dec. 10, 2015

Related U.S. Application Data

(60) Provisional application No. 61/753,036, filed on Jan. 16, 2013.

(51) Int. Cl.
*G01N 21/00* (2006.01)
*G01N 21/47* (2006.01)

(52) U.S. Cl.
CPC ..... *G01N 21/4738* (2013.01); *G01N 2201/065* (2013.01); *G01N 2201/0642* (2013.01)

(58) Field of Classification Search
CPC G01N 15/0227; G01N 21/532; G01N 21/474; G01N 2201/065; G01N 21/276; G01N 33/18; G01N 21/59; G01N 2015/0294; G01N 2015/0693; G01N 2021/1793; G01N 2021/1797; G01N 21/05; G01N 21/251
See application file for complete search history.

(56) References Cited

U.S. PATENT DOCUMENTS

| 2002/0018203 A1* | 2/2002 | Battle | G01J 3/02 356/319 |
| 2009/0079987 A1* | 3/2009 | Ben-Ezra | G01N 21/474 356/445 |

(Continued)

FOREIGN PATENT DOCUMENTS

CN 202101836 1/2012 ............ G01M 11/02

OTHER PUBLICATIONS

PCT/CA2014/000026 Search Report dated Apr. 7, 2014.

*Primary Examiner* — Michael P Stafira
(74) *Attorney, Agent, or Firm* — Teitelbaum & MacLean; Neil Teitelbaum; Doug MacLean (57) ABSTRACT

The invention relates to a light integrating cavity device, such as an integrating sphere, for measuring diffuse reflectance of a sample. A light trap is movable within a light scattering cavity of the device for controlling specular reflections during measurements. The light trap may be rotatable around the sample under test inside the cavity so that specular reflections off the sample can be included or excluded from the measurement. The sample may also be placed at the outside against a measurement port, and a measurement instrument is moveable on a rotating arm within or outside of the cavity.

17 Claims, 10 Drawing Sheets

(56) References Cited

U.S. PATENT DOCUMENTS

2015/0260648 A1* 9/2015 Xu .................. G01N 21/59
                                                  356/218
2015/0359951 A1* 12/2015 Andersen ............ A61M 1/0088
                                                  604/319

* cited by examiner

INTEGRATING SPHERE TYPE DEVICE WITH SPECULAR CONTROL

RELATED APPLICATION DATA

This application is the national stage entry of International Appl. No. PCT/CA2014/000026, filed Jan. 16, 2014, which claims priority to U.S. Provisional Patent Application No. 61/753,036, filed Jan. 16, 2013. All claims of priority to these applications are hereby made, and each of these applications is hereby incorporated in its entirety by reference.

TECHNICAL FIELD

The present invention generally relates to an integrating sphere type device for reflectance measurements, and more particularly to such a device which includes a light trap within a light scattering cavity for measuring diffuse reflectance with the specular component included or excluded.

BACKGROUND OF THE INVENTION

An integrating sphere is an optical component that is formed of a hollow spherical or hemispherical cavity with its interior covered with a diffusely reflecting coating. The integrating sphere normally has holes on the sphere wall for measurement and for illumination of the sphere and surface. Light rays incident on any point on the inner surface are scattered via diffuse reflection. After many reflections the illumination on, and radiance from, all parts of the sphere wall is highly homogeneous. When an integrating sphere is used to measure a hemispherical reflectance of a surface, the surface under test (SUT) may be situated at the sample port, at an aperture on the sphere, or inside the sphere such that the surface is illuminated from all directions inside the sphere. The measurement of the light emitted or reflected from the surface is conventionally done through a separate measurement hole through the side of the sphere.

Figure 1:
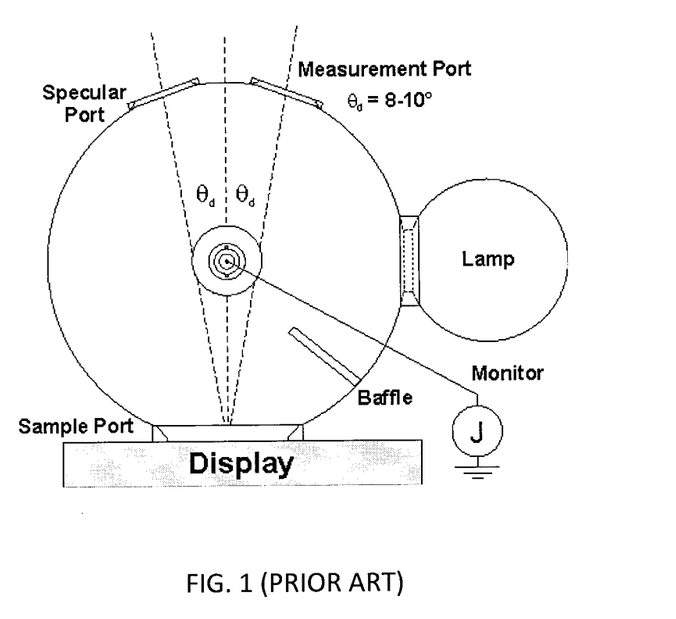
FIG. 1 is a schematic diagram of a conventional integrating sphere having a specular port in the sphere for reflectance measurements with specular component excluded.

One application for the integrating sphere is to simulate real-world illumination conditions upon displays of devices such as cell phones, tablets or televisions in order to evaluate their contrast ratios; see for example a publication of International Committee for Display Methodology (IDSM), entitled "Information Display Measurements Standard", version 1.03, Jun. 1, 2012, which is incorporated herein by reference. To make such a hemispherical reflection condition without the specular component, an additional hole is provided through the sphere which aligns to the position where the specular component of the reflection originates, as illustrated for example in FIG. 1, which reproduces FIG. 1 of Section 11.3.2, pg. 204, of the above cited publication. The location of the specular hole is exactly mirrored from the position where the measurement is taken, both with respect to the normal direction of the sample under test. Usually this specular port is directed into a dark room or a light trap that is external to the integrating sphere. To measure diffuse reflectance including the specular component, a filler plug must be used in place of the light trap.

This design has several limitations, including the following: a) only fixed angles of diffuse reflectance with the specular component excluded can be measured, b) the reflectance of the filler plugs may not be uniformly matched to the sphere wall and c) the radiance for highly mirror-like surfaces may be less accurately measured when the specular region is aligned to this non-uniform filler plug.

An objective of the present invention is to provide an improved integrating sphere type device that addresses at least some of the aforementioned limitations of conventional integrating sphere devices.

SUMMARY OF THE INVENTION

Accordingly, the present invention relates to a light integrating cavity device (LICD) for measurement of diffuse light reflectance of a sample, which comprises a shell enclosing a light scattering cavity (LSC) defined by an internal light scattering surface of the shell, and a light source disposed for illuminating the internal light scattering surface of the shell for creating scattered light within the LSC for illuminating the sample therewith. The shell has an aperture for allowing light out of the light scattering cavity for illuminating the sample when the sample is positioned at the aperture outside of the LSC, or for illuminating a light measurement device (LMD) with the scattered light reflected from, or transmitted through, the sample when the LMD is positioned outside of the LSC facing the aperture. A light trap is further provided that is mounted within the LSC and is rotatable to be in a specular optical alignment with the sample and the LMD, so as to prevent the LMD from receiving specular reflections from the sample.

Another aspect of the present invention relates to a method of measuring a diffuse light reflectance of a sample using a light integrating cavity device for providing diffuse light upon the sample and a light measurement device for measuring reflectance of the diffuse light from the sample, the method comprising: a) providing a movable light trap within a light integrating cavity of the light integrating cavity device, and b) moving the light trap to a position of a specular alignment with the sample and the light measurement device so as to prevent the light measurement device from receiving specular reflections from the sample.

One exemplary implementation of the LICD includes a suitable mechanism that enables rotation of the light trap around the sample under test inside of the integrating sphere. The light trap can be positioned to the specular reflection location with respect to the sample under test and the measurement instrument in order to eliminate the specular reflection component from the measurement, or the light trap may be positioned such that it has a different effect upon the measurement.

One exemplary implementation of LICD permits the mounting and measurement of a reflecting or transmitting sample at the side of a shell of the device. This implementation may employ a "partial sphere" shell and is referred to in that case as the "partial sphere" configuration. A light trap on a rotatable post and a measurement instrument on another rotatable post within the shell may be used in this implementation to measure diffuse reflectance or transmittance of the sample, with and without the specular component.

BRIEF DESCRIPTION OF THE DRAWINGS

The invention will be described in greater detail with reference to the accompanying drawings which represent preferred embodiments thereof, in which like elements are indicated with like reference numerals, and wherein.

DETAILED DESCRIPTION

In the following description, for purposes of explanation and not limitation, specific details are set forth, such as particular circuits, sub-systems, optical and circuit components, mechanical elements, assemblies, or techniques, etc. in order to provide a thorough understanding of the present invention. However, it will be apparent to one skilled in the art that the present invention may be practiced in other embodiments that depart from these specific details. In other instances, detailed descriptions of well-known methods, devices, and tools are omitted so as not to obscure the description of the present invention.

Note that as used herein, the terms "first", "second" and so forth are not intended to imply sequential ordering, but rather are intended to distinguish one element from another unless explicitly stated.

Figure 2:
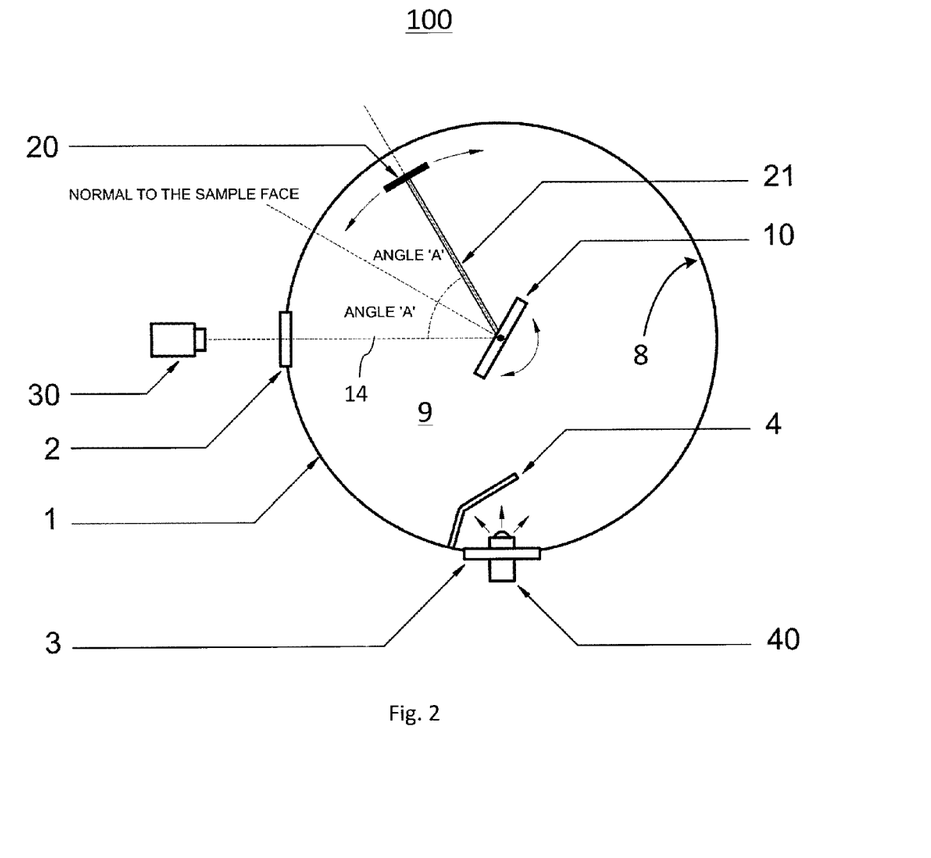
FIG. 2 is a schematic top view of a "whole-sphere" ISTD with an internal light trap positioned for excluding the specular reflection component.

With reference to FIG. 2, there is shown a schematic top view of an integrating sphere type device (ISTD) 100 representing one exemplary "whole sphere" embodiment of a light integrating cavity device (LICD) of the present invention. A spherical shell 1 has an internal light scattering surface 8 with a diffusely reflecting coating thereon as known in the art of integrating spheres. The interior of the shell 1 bounded by the internal light scattering surface 8 thereof forms a light scattering cavity (LSC) 9. A sample 10 is positioned within the LSC 9 with its face, which reflectance is to be tested, oriented towards an aperture 2 at a variable angle 'A". The aperture 2, which is also referred to herein as the measurement port 2, allows light that is reflected by the sample 10 towards the aperture to reach a light measurement device (LMD) 30, which in this embodiment is positioned outside of the ISDT 100 facing the aperture and is optically aligned with the sample 10. A light source 40 is provided for illuminating the internal light scattering surface 8 of the shell 1 and for creating scattered light within the LSC 9. Preferably, light from the light source 40 illuminates the inside of the shell 1 such that the luminance, or radiance, of all parts of the internal light scattering surface 8, as seen from the location of the sample 10 positioned within the LSC 9, is quite homogeneous. In the shown embodiment, the light source 40 is mounted in a light source port 3 that may be in the form, or include, an aperture or opening in the shell 1. The light source 40 may be in the form of any suitable artifact of white or colored light as known in the art. A shield or baffle 4 may further be provided to prevent the sample 10 and the aperture 2 from being illuminated by the light source 40 directly without scattering.

In accordance with a feature of the present invention, a light trap 20 is provided within the LSC 9 and is positionable in the plane of measurement so as to prevent selected angles of scattered light from being reflected by the sample 10 into the aperture 2 ensuring that they won't be measured by the measurement device 30. The term 'plane of measurement', which coincides with the plane of the figure, refers to a plane that is normal to the face of the sample 10 and includes the aperture 2 and LMD 30. The light trap 20 is preferably made of a very low reflectance material so it absorbs most of the light incident thereon substantially without reflecting. Examples of such materials include, but not limited to, black flock paper, black masking tape black aluminum foil, matte black paint, carbon nanotubes, stacked razor blades (as viewed straight at the stacked cutting edges), commercially available light absorbing foils and vapor deposited materials.

In particular, FIG. 2 shows the light trap 20 being in a position of a specular alignment with the aperture 2 and the sample 10, wherein the light trap 20 prevents the LMD 30 from receiving specular reflections from the sample 10. More particularly in FIG. 2, a sample 10 is tilted to angle "A" relative to a measurement axis 14, and the light trap 20 is rotated to twice the angle "A" relative to the measurement axis. At these orientations, the light trap 20 is at the specular reflection angle for the measurement, meaning that it blocks the LMD 30 from receiving specular reflections off the sample 10. Since the light trap 20 has very low luminance or radiance compared to the interior surface 8 of the sphere 1, the measurement by the measurement instrument 30 in the configuration of FIG. 2 is said to be "excluding the specular component", or to be "specular excluded".

In one embodiment, the light trap 20 is mounted on a rotatable arm 21, which is also referred to as the light trap post 21 and which can be rotated so as to bring the light trap 20 in and out of the specular alignment with the sample 10 and the aperture 2 and/or the LMD 30. In one embodiment the rotatable arm 21 can be rotated in the plane of measurement so that the sample 10 can be brought into the position of specular alignment for various angular orientations of the sample 10, i.e. for varying angle 'A', in 'specular excluded' measurements.

Figure 3:
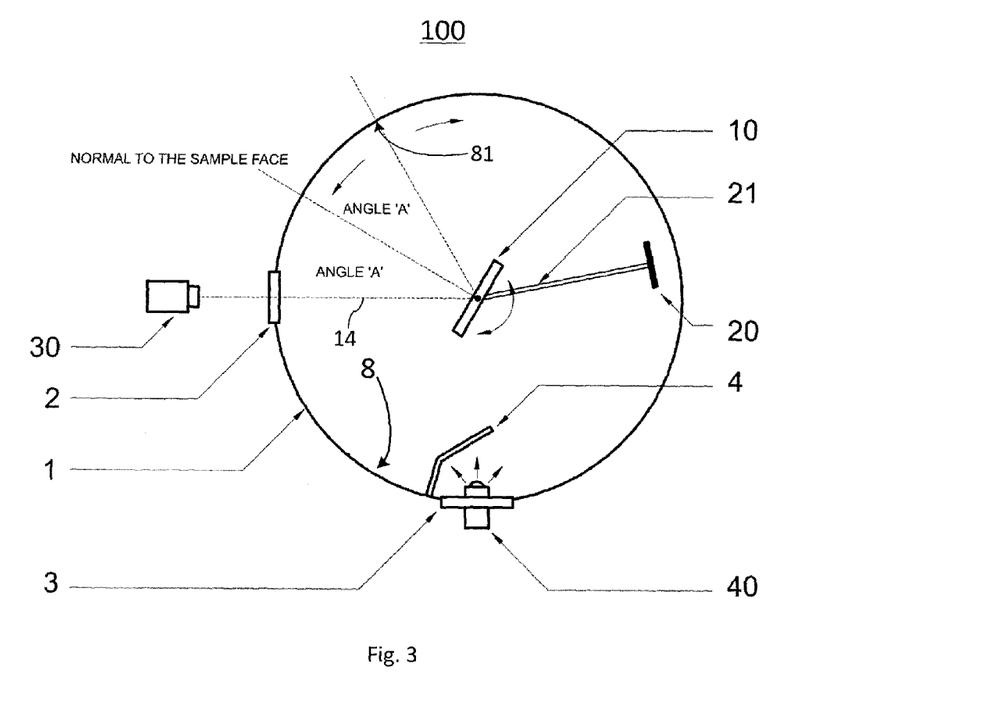
FIG. 3 is a schematic top view of the "whole-sphere" ISTD of FIG. 2 with the internal light trap positioned for including the specular reflection component.

Turning now to FIG. 3, it shows by way of example how the light trap 20 may be repositioned by rotating the arm 21 so that the light trap 20 is behind the reflecting surface of the sample 10. With such a position of the light trap 20, a portion 81 of the high-luminance interior sphere surface 8, which is at the specular angle 2A from the measurement axis 14, is visible from the LMD 30, which is now able to measure the sample reflectance with the specular component included, i.e. to perform the 'specular included' measurement.

Figure 4:
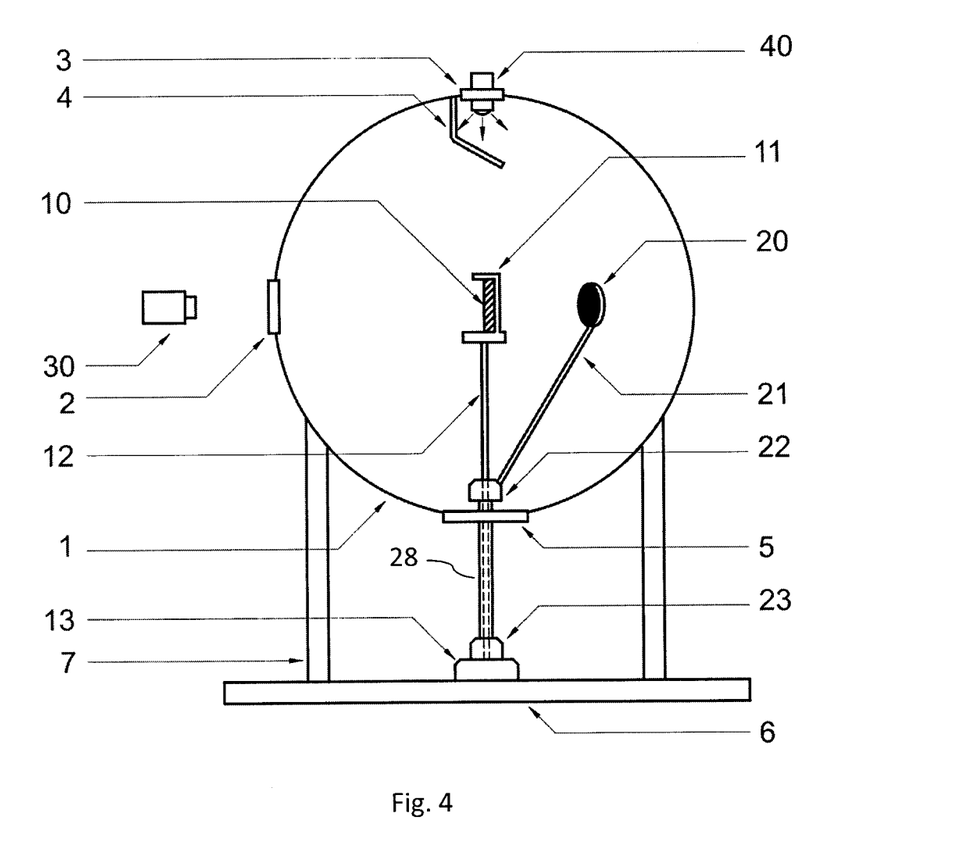
FIG. 4 is a schematic side view of one implementation of the ISTD of FIG. 2.
Figure 8:
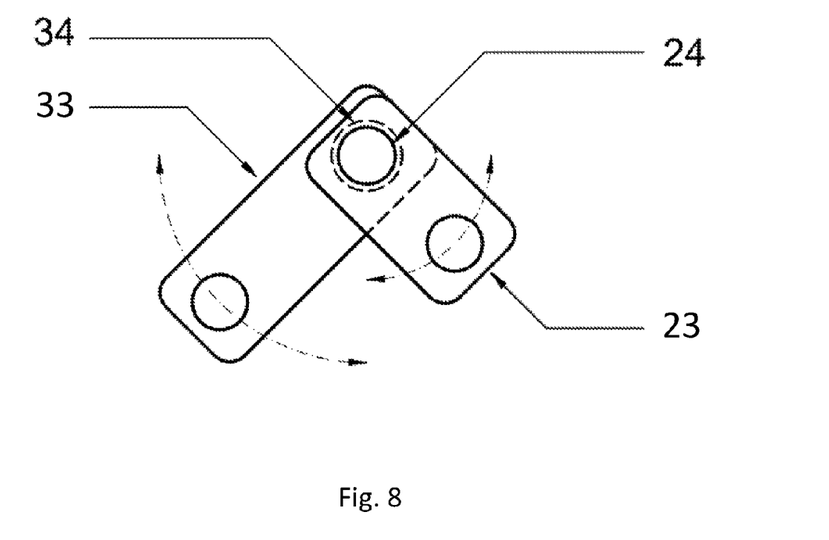
FIG. 8 is a schematic view of a rotation sleeve termination for rotating the measurement device and light trap about the sample.

Referring now to FIG. 4, there is illustrated an embodiment of the ISTD 100 wherein the sample 10 and the light trap 20 may be rotated from outside of the shell 1. It includes a support member 11 in the form of a sample stage for supporting, i.e. rotatably holding, the sample 10 facing the aperture 2 at a desired angle, enabling the sample to be rotated about an axis thereof. In one embodiment, the sample 10 is mounted to the sample stage 11 at the center of the spherical interior of the shell 1, and the sample stage 11 is attached to a sample post 12 and can be rotated from outside the shell by rotating the sample post 12. A sample rotation stage 13 may be provided for rotating the sample post 12, and therefore the sample stage 11, thereby rotating the sample 10 and turning its reflective surface at various angles to the aperture 2 and thus the measurement device 30. Various implementations of the sample rotation stage 13 may be readily envisioned by a skilled technician. By way of example, it may be in the form of a friction sleeve, such as illustrated in FIG. 8, for manual positioning of the sample; it may also be a motorized stage for computer and electrically driven control of the sample position and/or orientation.

Continuing to refer to FIG. 4, the light trap 20 is attached to the light trap arm 21, so that the light trap 20 is rotatable about the sample 10 in the plane of the measurement. In one embodiment, the light trap arm 21 is attached to a pole 28 that is rotatable from outside of the shell 1. In one embodiment, the light trap pole 28 is coaxial with the sample post 12, such as in the form of a sleeve, and at the outside of the shell 1 it is further mechanically coupled to a light trap rotation stage 23, which by way of example may be either a friction sleeve for manual positioning, such as shown in FIG. 8, or a motorized stage for computer and electrically driven control of the light trap position.

The light trap 20 is preferably designed to have minimal reflection so as to have minimal luminance and radiance under illumination inside the sphere as compared to that of the internal surface 8 of the shell 1. By way of example, the light trap 20 could be constructed of a disk with a light absorbing coating. In another example, the light trap 20 could have a conical geometry with a glossy black interior, providing very little reflection in the direction normal to the trap.

The light source 3 may be positioned anywhere in the sphere such that it does not directly illuminate the sample or measurement instrument. More than one light source 3 may be employed in the sphere. The requirement, design, and positioning of the baffle(s) 4 depends upon the light source (s) 3 employed as would be evident to those skilled in the art. The main function of the baffle(s) 4 is to prevent direct illumination of the sample 10 and measurement instrument 30. The interior of the sphere 1 has a uniform, highly reflective and diffuse coating such that light scattering inside the sphere is optimized and the luminance on the inside of the sphere 1 is optimally uniform. In one embodiment, the shell 1 may be mounted on a base 6 using shell supports 7.

Figure 5:
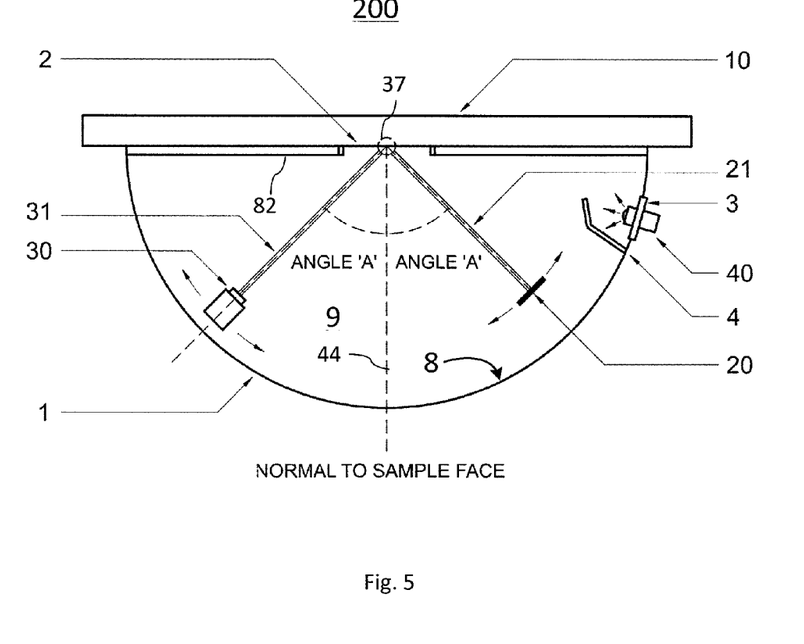
FIG. 5 is a schematic top view of a "partial sphere" ISTD with an internal light trap positioned for reflectance measurements excluding the specular reflection component.
Figure 6:
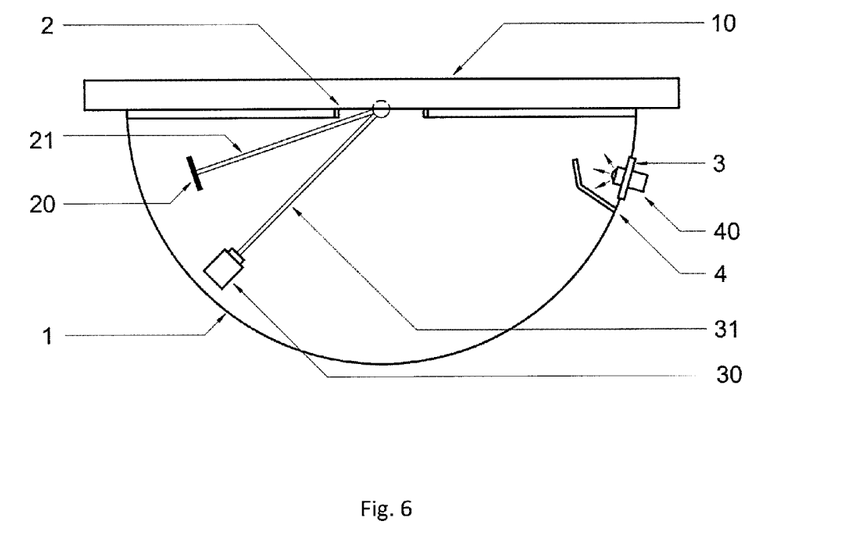
FIG. 6 is a schematic top view of the "partial sphere" ISTD with the internal light trap positioned for reflectance measurements including the specular reflection component.

Turning now to FIGS. 5 and 6, there is shown a schematic top view of ISTD 200, which represents an exemplary "partial sphere" embodiment of the LICD of the present invention for measuring diffuse reflectance of a sample. Similarly to ISTD 100, the 'partial sphere' ISDT 200 includes the light trap 20 disposed inside the LSC 9 for enabling the 'specular included' and 'specular excluded' types of measurements. Similarly to the ISTD 100, in a preferred embodiment of the ISTD 200 the light trap 20 is rotatably mounted to a light trap arm 21 so that it may be moved in the measurement plane to include or exclude the specular reflection. FIG. 5 shows the light trap 20 oriented to the 'specular excluded' geometry. FIG. 6 shows the ISTD 200 with the light trap 20 oriented for 'specular included' measurements. However, the ISTD 200 differs from ISTD 100 in the shape of the shell 1, the shape of the LSC 9, and the positioning of the sample 10 and the LMD 30 during measurements.

In the illustrated embodiment, the shell 1 is of substantially semi-spherical shape and includes a flat portion or wall 82, wherein the measurement aperture or port 2 is located. During measurements the sample 10 is positioned at the aperture 2 outside of the shell 1 facing the aperture 2. In this embodiment, the measurement aperture 2 is for allowing light from the LSC 9 to illuminate the sample 10 and for allowing the light scattered or reflected from the sample 10 back into the LSC 9. The flat portion 82 of the shell 1 provides support for the sample. In other embodiments, the flat portion 82 of the shell 1 may have a different shape, for example depending on a desired measurement configuration and sample shape. The interior of the shell 1 forms the LSC 9 which may also be of a generally semispherical shape.

The measurement device 30 is now positioned within the LSC 9, and in a preferred embodiment, is movable inside the LSC 9, while the light trap 20 may also move within the plane of measurement. The LMD 30 may be a photometer, colorimeter, spectroradiometer, or other similar light detector or imaging instrument. In one embodiment, the LMD 30 may be in the form of an end of an optical fiber or a fiber-optic cable, with a suitable photodetecting device optically coupled to the other end thereof and positioned outside of the "partial sphere" shell 1.

Continuing to refer to FIGS. 5 and 6, in this embodiment the light source 3 may be positioned anywhere in the partial sphere 9 such that it does not directly illuminate neither the sample 10, nor the measurement device 30, nor the light trap 20. More than one light source 3 may be employed to illuminate the interior surface 8 of the shell 1. The requirement and design and positioning of the baffle(s) 4 depend upon the light source(s) 3 employed. The main function of the baffle(s) 4 is to prevent direct illumination of the sample 10 and measurement instrument 30. The interior surface 8 of the semi-spherical part of the shell 1 has a uniform, preferably highly reflective and diffuse coating such that light scattering inside the semi-sphere is optimized and the luminance on the interior surface 8 of the shell 1 is optimally uniform.

In one embodiment, the LMD 30 is attached to a support member 31 in the form of a rotatable LMD arm. Similar to ISTD 100, the light trap 20 is mounted to the rotatable arm 21. In one embodiment, the LMD arm 31 and the light trap arm 21 are rotatable about the same rotation axis 37 that is normal to the measurement plane, which is the plane of FIGS. 5 and 6, and in one embodiment is preferably at or near the aperture 2 or more preferably, at or near the surface of the sample 10 which reflectance is to be measured. The LMD arm 31 may be rotated so as to receive light reflected from the sample 10 at various angles. In one embodiment, the angular rotation range of the LMD arm 31 may be close to +\−90 degrees, enabling 180 degrees of angular reflectance measurements.

The light trap 20 may be as described herein above with reference to ISTD 100, and is preferably designed to have minimal reflection (luminance and radiance) under illumination inside the hemispherical shell 1. The light trap 20 could be constructed of a disk with a light absorbing coating. In another example, the trap could have a tapered or conical geometry with a glossy black interior—providing very little reflection in the direction normal to the light trap 20.

In one embodiment the rotatable light trap arm 21 can be rotated in the plane of the measurement so that the light trap 20 can be brought into the position of specular alignment for various angular orientations of the LMD 30, so that the specular reflections from the sample 10 into the LMD 30 may be blocked for a plurality of positions of the LMD 30, i.e. for varying angle 'A', thereby enabling the 'specular excluded" measurement as illustrated in FIG. 5, or to turn the light trap 20 away from the specular alignment with the LMD 30 and the aperture 2 and sample 10, for example as illustrated in FIG. 6, for performing the 'specular included" measurement.

Figure 7:
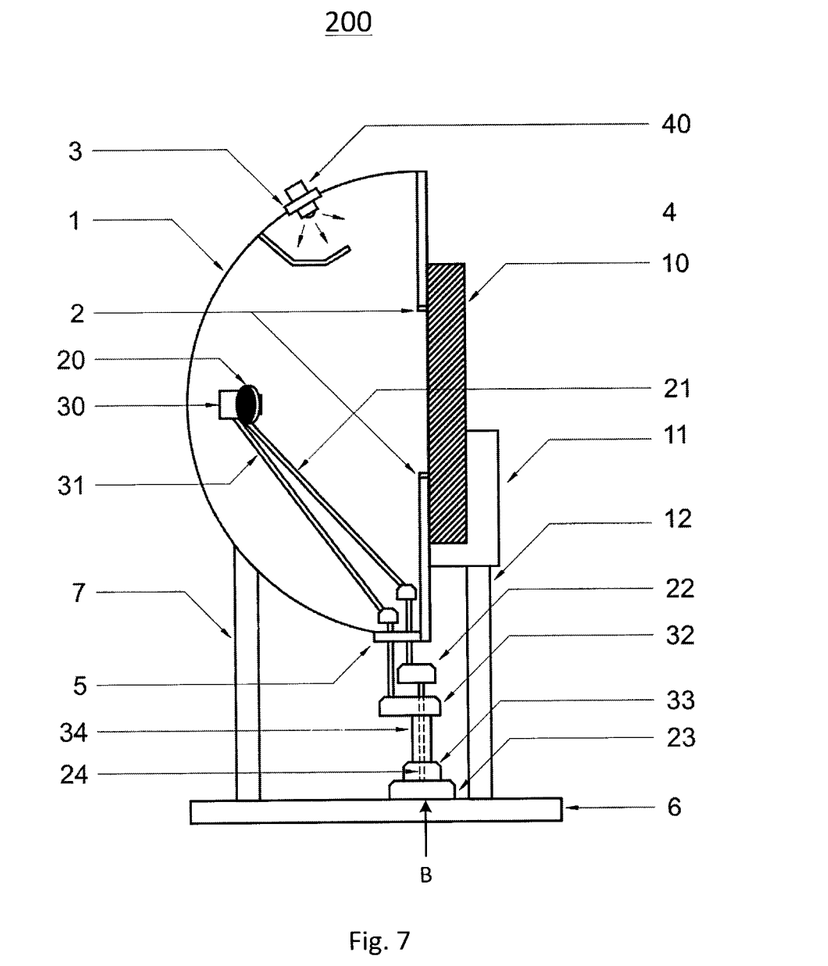
FIG. 7 is a schematic side view of one implementation of the "partial sphere" ISTD of FIG. 5.

Referring now to FIG. 7, there is shown a side view of an embodiment of the ISTD 200 including a rotation assembly that enables rotating the LMD 30 and the light trap 20 from outside of the shell 1. In the shown exemplary embodiment, this rotation assembly includes a LMD rotation pole 34 coupled with the LMD rotation arm 31 by means of a LMD arm rotation assembly 32, and a light trap rotation pole 24 coupled with the light trap rotation arm 21 by means of a light trap arm rotation assembly 22. In one embodiment, the LMD rotation pole 34 is coaxial with the light trap rotation pole 24, with one or the other being in the form of a sleeve in which the other can be freely rotated. The shell 1 includes a rotation assembly port 5 located at the flat portion of the shell through which the rotation pole assembly may be inserted.

In one embodiment, the LMD rotation pole 34 is coupled to a LMD rotation pole termination 33, by means of which the LMD 30 may be rotated about the rotation axis of measurement 37. The light trap 20 may be rotated about the axis of measurement 37 using the light trap rotation pole termination 23 attached thereto. The rotation pole terminations 23 and 33 may be in the form of, for example, friction sleeves for manual positioning, or may be motorized stages for computer and electrically driven control of the sample position. In one embodiment the shell 1 is supported on a base 6 using shell supports 7. A sample stage 11 may further be provided for holding the sample 10 against the measurement port or aperture 2, and may be supported on the base 6 by a sample support post 12. Various other support configurations for supporting the shell 1 and the sample 10 therewithin will be evident to those skilled in the art, and are within the scope of the present invention.

Turning now to FIG. 8, there is illustrated a view of the rotation pole terminations 23, 33 when looking in the direction illustrated in FIG. 7 by arrow B, in a 'rotation sleeve' embodiment. In this embodiment, the rotation pole terminations 23, 33 may be manually rotated so as to rotate the LMD 30 and the light trap 20 within the LSC 9.

One advantage of the ISTD 200 over the ISTD 100 is that it can be smaller in size to perform the diffuse reflectance measurements of similar samples.

Figure 9:
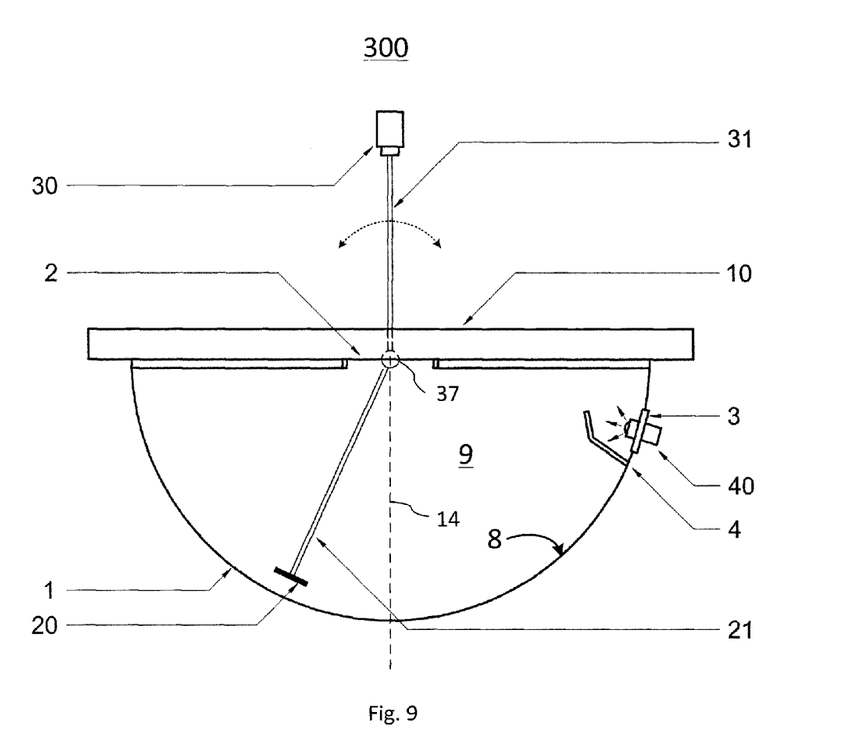
FIG. 9 is a schematic top view of the "partial sphere" ISTD configured for diffuse transmission measurements.

Referring now to FIG. 9, there is shown a schematic top view of the ICTD 300, which represents another exemplary "partial sphere" embodiment of the LICD of the present invention for measuring diffuse transmission of a sample. The ISTD 300 has a "partial sphere" shape that is similar to that of the ISTD 200. One difference from the ISTD 200 is that the LMD 30 is now positioned externally to the partial sphere shell 1 behind the sample 10, which is being measured in transmission mode. Similarly to the ISTD 200, the "partial sphere" ISDT 300 includes the light trap 20 mounted inside the LSC 9 on a rotatable arm 21 for rotating the light trap to enable positioning thereof for blocking a selected angle of incidence of the scattered light upon the sample 10, and for enabling the 'specular included' and 'specular excluded' types of measurements. The ISTD 300 may be obtained from the ISTD 200 by moving the LMD rotation pole assembly and the LMD rotation arm 31 outside of the shell 1 behind the sample 10.

For the 'specular excluded' measurements, the light trap 20 may be positioned inside the LSC 9 on the axis of measurement 14. In this way, only light scattered by the sample under test will be measured by the LMD 30, while the light trap 20 blocking light that would have otherwise passed from the LSC 9 through the sample 10 and onto the LMD 30 without being scattered by the sample 10. The angle of the axis of measurement 14 with respect to the sample 10 can by altered by rotating the LMD rotation arm 31 with the LMD 30 attached thereto using the instrument rotation stage or termination 33.

Figure 10:
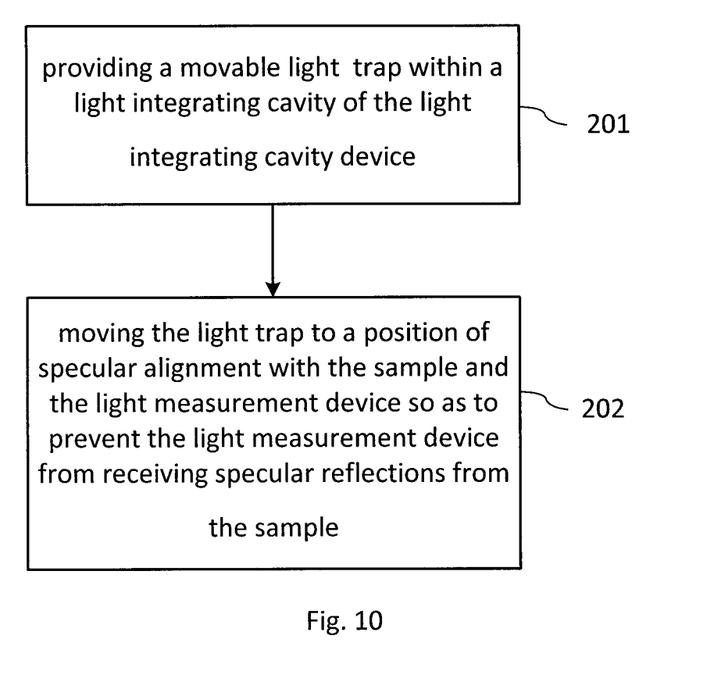
FIG. 10 is a flowchart of a method for measuring a diffuse reflectance of a sample with specular control using a movable light trap within a light scattering cavity according to an embodiment of the present invention.

Turning now to FIG. 10, one aspect of the present invention provides a method of measuring a diffuse light reflectance of a sample using a light integrating cavity device, such as but not exclusively those illustrated in FIGS. 2-7 and 9, for providing diffuse light upon the sample and a light measurement device for measuring reflectance of the diffuse light from the sample, which includes the following general steps or actions:

A) providing a movable light trap 20 within a light integrating cavity 9 of the light integrating cavity device at 201, and b) moving the light trap to a position of a specular alignment with the sample 10 and the light measurement device so as to prevent the light measurement device from receiving specular reflections from the sample at 202.

Advantageously, all of the exemplary embodiments described hereinabove of the integrating cavity device of the present invention substantially simplify variable-angle measurements of the sample reflectance with the specular component excluded, while enabling a uniform luminance distribution across the interior surface of the LSC by eliminating the need for a light trap aperture plug. Although in a preferred embodiment the light trap within the shell 1 is movable, embodiments wherein the light trap is located at a fixed position within the shell are also within the scope of the present invention. In accordance with another advantageous feature of the present invention, the light trap 20 may be removed from the interior 9 of the shell 1 and replaced with another light trap that may have, for example, a different shape or size.

The above-described exemplary embodiments are intended to be illustrative in all respects, rather than restrictive, of the present invention. Thus the present invention is capable of many variations in detailed implementation that can be derived from the description contained herein by a person skilled in the art. For example, while the exemplary embodiments described hereinabove use spherical or semi-spherical shells, other embodiment's may utilize shells of different type such as but not exclusively, that of an ovoid or a box. Furthermore, in other embodiments the interior surface of the shell may be a whole or a partial sphere, the exterior of the shell may be of any suitable shape, such as for example a box. Still further, many other variations of the shell support means and means for rotating the sample, light trap and/or measurement device may be envisioned. All such and other variations and modifications are considered to be within the scope and spirit of the present invention as defined by the following claims.

I claim:

1. A light integrating cavity device (LICD) for measurement of diffuse light reflectance of a sample, the LICD comprising:
   a shell enclosing a light scattering cavity (LSC) defined by an internal light scattering surface of the shell;
   a light source disposed for illuminating the internal light scattering surface of the shell for creating scattered light within the LSC for illuminating the sample therewith,
   wherein the shell has an aperture for allowing light out of the light scattering cavity for illuminating the sample when the sample is positioned at the aperture outside of the LSC, or for illuminating a light measurement device (LMD) with the scattered light reflected from the sample or transmitted through the sample when the LMD is positioned outside of the LSC facing the aperture;

a light trap mounted within the LSC and positionable in a specular optical alignment with the sample and the LMD so as to prevent the LMD from receiving specular reflections from the sample; and a light trap arm movably mounted within the LSC for supporting the light trap and for moving the light trap in and out of a position of the specular optical alignment with the sample and the LMD, so as to allow the diffuse light reflectance of the sample to be measured by the LMD with the specular component of the reflectance included and with the specular component of the reflectance excluded.

2. The LICD of claim 1, wherein the aperture is for allowing light from the LSC to illuminate the sample when the sample is disposed outside of the LSC facing the aperture and for allowing the light reflected from the sample back into the LSC, the LICD further comprising an LMD arm rotatably mounted within the LSC for positioning the LMD within the LSC facing the aperture at various angles for measuring the light reflected from the sample, and wherein the light trap arm is rotatably mounted within the LSC for rotating the light trap to enable positioning of the light trap in the specular alignment with the sample and the LMD for excluding specular reflections from the sample from being received by the LMD during the measuring.

3. The LICD of claim 2, further comprising a sample stage for holding the sample against the aperture.

4. The LICD of claim 2, wherein the LCS is generally semi-spherical in shape defined by a semispherical portion of the inner surface and a plane portion thereof, and wherein the plane portion includes the aperture.

5. The LICD of claim 4, further comprising a rotation assembly for rotating the LMD and light trap arms from outside the LSC.

6. The LICD of claim 5, wherein the rotation assembly comprises a rotation pole assembly comprising an LMD rotation pole coupled with the LMD rotation arm and a light trap rotation pole coupled with the light trap rotation arm.

7. The LICD of claim 6, wherein the LMD rotation pole is coaxial with the light trap rotation pole.

8. The LICD of claim 5 wherein the shell comprises a rotation assembly port for accepting the rotation pole assembly.

9. The LICD of claim 6 wherein the rotation assembly further comprises an LMD pole termination and a light trap pole termination for enabling the rotation pole assembly to rotate the LMD and light trap arms from outside of the shell.

10. The LICD of claim 1, wherein the aperture is for allowing the scattered light from the LSC to illuminate the sample disposed outside of the LSC and to be transmitted through the sample onto the LMD when the LMD is disposed optically behind the sample, and wherein the light trap arm is rotatably mounted within the LSC for rotating the light trap to enable positioning thereof for blocking a selected angle of incidence of the scattered light upon the sample.

11. The LICD of claim 10, further comprising an LMD arm rotatably mounted outside of the LSC for holding the LMD optically behind the sample facing the aperture and for rotating the LMD for measuring light transmitted though the sample at various angles.

12. The LICD of claim 1, wherein the aperture is for allowing light from the LSC to illuminate the sample disposed outside of the LSC and to be transmitted through the sample onto the LMD disposed optically behind the sample, and wherein the light trap arm is rotatably mounted within the LSC for rotating the light trap to enable positioning thereof for blocking light that would have otherwise passed from the LSC through the sample and onto the LMD without being scattered by the sample.

13. The LICD of claim 1, wherein the aperture is for allowing light from the LSC to illuminate the LMD when the LMD is disposed outside of the LSC facing the aperture, the LICD further comprising a rotatable sample holder for holding the sample within the LSC in a position where the sample reflects the scattered light towards the aperture and for rotating the sample about an axis thereof so as to vary an angle of the sample relative to the aperture and the LMD;

wherein the light trap arm is rotatably mounted within the LSC for rotating the light trap about the sample to enable positioning of the light trap in the specular alignment with the sample and the aperture for excluding specular reflections from the sample from being received by the LMD during the measuring for a plurality of angular sample orientations.

14. The LICD of claim 13, further comprising a rotation assembly for rotating the sample holder and the light trap arm from outside the shell.

15. The LICD of claim 14, wherein the rotation assembly comprises a coaxial rotation pole assembly comprising a sample rotation pole and a light trap arm rotation pole coaxial therewith.

16. The LICD of claim 14, wherein the shell comprises a rotation assembly port for accepting the rotation assembly to extend from outside of the shell into the LSC.

17. A method of measuring a diffuse light reflectance of a sample using a light integrating cavity device for providing diffuse light upon the sample and a light measurement device for measuring reflectance of the diffuse light from the sample, the method comprising:

providing a movable light trap within a light integrating cavity of the light integrating cavity device, and moving the light trap to a position of a specular alignment with the sample and the light measurement device so as to prevent the light measurement device from receiving specular reflections from the sample.

* * * * *